US012751602B2

(12) United States Patent
Bi

(10) Patent No.: US 12,751,602 B2
(45) Date of Patent: Oct. 6, 2026

(54) DISPOSABLE ENDOSCOPE DRIVE

(71) Applicant: Covidien LP, Mansfield, MA (US)

(72) Inventor: Chenghao Bi, Boulder, CO (US)

(73) Assignee: Covidien LP, Mansfield, MA (US)

( * ) Notice: Subject to any disclaimer, the term of this patent is extended or adjusted under 35 U.S.C. 154(b) by 190 days.

(21) Appl. No.: 18/600,914

(22) Filed: Mar. 11, 2024

(65) Prior Publication Data

US 2024/0341576 A1 Oct. 17, 2024

Related U.S. Application Data

(60) Provisional application No. 63/495,373, filed on Apr. 11, 2023.

(51) Int. Cl.

*A61B 1/00* (2006.01)
*A61B 1/005* (2006.01)
*A61M 25/01* (2006.01)

(52) U.S. Cl.

CPC ........ *A61B 1/0016* (2013.01); *A61B 1/00103* (2013.01); *A61B 1/00124* (2013.01); *A61B 1/0057* (2013.01); *A61M 25/0147* (2013.01)

(58) Field of Classification Search

CPC .............. A61B 1/0016; A61B 1/00103; A61B 1/00124; A61B 1/0057; A61B 34/30; A61B 34/71

See application file for complete search history.

(56) References Cited

U.S. PATENT DOCUMENTS

| | | | | |
|---|---|---|---|---|
| 5,469,840 | A | 11/1995 | Tanii et al. | |
| 2002/0062062 | A1 | 5/2002 | Belson et al. | |
| 2004/0242966 | A1* | 12/2004 | Barry | A61B 1/0057 600/146 |
| 2014/0121462 | A1* | 5/2014 | Okamoto | A61B 1/00042 600/152 |
| 2015/0011830 | A1* | 1/2015 | Hunter | A61B 1/0016 600/118 |

(Continued)

FOREIGN PATENT DOCUMENTS

| | | | |
|---|---|---|---|
| EP | 2 324 755 | B1 | 7/2012 |
| WO | 2022/133248 | A1 | 6/2022 |

(Continued)

OTHER PUBLICATIONS

International Search Report for International Application No. PCT/IB2024/053438 mailed Jul. 11, 2024 (13 pages).

(Continued)

*Primary Examiner* — Timothy J Neal

(57) ABSTRACT

The technology relates to an endoscope having a proximal end and a distal end with a steerable distal tip. The endoscope may include a motor positioned within an interior of the endoscope, the motor comprising an axle; a drum connected to the axle such that rotation of the axle causes rotation of the drum; an anchoring cylinder affixed to an interior surface of the endoscope; a first pull wire coupled to the drum and affixed to the anchoring cylinder, such that rotation of the drum in a first direction causes the first pull wire to wind around the drum; and a second pull wire coupled to the drum and affixed to the anchoring cylinder, such that rotation of the drum in a second direction causes the second pull wire to wind around the drum.

15 Claims, 5 Drawing Sheets

(56) References Cited

U.S. PATENT DOCUMENTS

| | | | | |
|---|---|---|---|---|
| 2020/0254204 | A1 | 8/2020 | Moffat et al. | |
| 2023/0309801 | A1* | 10/2023 | Christensen | A61B 1/0057 600/146 |

FOREIGN PATENT DOCUMENTS

| | | | |
|---|---|---|---|
| WO | 2022/195695 | A1 | 9/2022 |
| WO | 2022/266500 | A1 | 12/2022 |

OTHER PUBLICATIONS

Final Office Action received for U.S. Appl. No. 18/630,573, mailed on Jun. 22. 2026, 19 pages.

* cited by examiner

DISPOSABLE ENDOSCOPE DRIVE

CROSS-REFERENCE TO RELATED APPLICATION

The present application claims the benefit of U.S. Provisional Patent Application Ser. No. 63/495,373, filed on Apr. 11, 2023, the entire content of which is incorporated herein by reference.

BACKGROUND

Laryngoscopes are commonly used to perform intubations on patients who require breathing assistance. During an intubation, the laryngoscope may be used to manipulate the anatomy of the larynx and associated structures of a patient's airway, in order to obtain a view sufficient for insertion of a breathing tube (e.g., an endotracheal tube) into the trachea. In some situations, the anatomy of the patient, or injury or other health condition of the patient, may prevent a clinician from obtaining a clear view of the larynx. In situations where intubation of a patient may be difficult, an endoscope may be used to aid visualization of the larynx and insertion of the breathing tube. An endoscope is a narrow, flexible tube that typically includes a light and camera at an insertable end of the tube and is inserted into the body for visualizing anatomical structures of a patient. The use of an endoscope may assist the clinician in performing an intubation.

It is with respect to this general technical environment that aspects of the present technology disclosed herein have been contemplated. Furthermore, although a general environment is discussed, it should be understood that the examples described herein should not be limited to the general environment identified herein.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

In an aspect, the technology relates to an endoscope having a proximal end and a distal end with a steerable distal tip. The endoscope includes a motor positioned within an interior of the endoscope, the motor comprising an axle; a drum connected to the axle such that rotation of the axle causes rotation of the drum; an anchoring cylinder affixed to an interior surface of the endoscope; a first pull wire coupled to the drum and affixed to the anchoring cylinder, such that rotation of the drum in a first direction causes the first pull wire to wind around the drum; and a second pull wire coupled to the drum and affixed to the anchoring cylinder, such that rotation of the drum in a second direction causes the second pull wire to wind around the drum.

In an example, the drum includes a first winding port through which the first pull wire is threaded; and a second winding port through which the second pull wire is threaded. In a further example, the anchoring cylinder includes a first anchoring port through which the first pull wire is threaded; and a second anchoring port through which the second pull wire is threaded. In another example, the first pull wire and the second pull wire are affixed to the anchoring cylinder with an adhesive. In yet another example, the endoscope further comprises an electrical interface positioned proximal from the motor. In still another example, a maximum diameter of the motor is less than 6 mm.

In another aspect, the technology relates to an endoscope that includes a proximal end housing a drive system; a distal end including a steerable distal tip; a first pull wire having a proximal end, coupled to the drive system, and a distal end affixed to the steerable distal tip; and a second pull wire having a proximal end, coupled to the drive system, and a distal end affixed to the steerable distal tip. The drive system includes a motor positioned within an interior of the endoscope, the motor comprising an axle and a drum connected to the axle such that rotation of the axle causes rotation of the drum. The proximal ends of the first pull wire and the second pull wire are coupled to the drum; rotation of the drum in a first direction causes the distal tip to bend in a first direction; and rotation of the drum in a second direction cause the distal tip to bend in a second direction.

In an example, the drum includes a first winding port through which the first pull wire is threaded; and a second winding port through which the second pull wire is threaded. In another example, the endoscope further includes an anchoring cylinder affixed to the endoscope, wherein the proximal ends of the first pull wire and the second pull wire are affixed to the anchoring cylinder. The anchoring cylinder includes a first anchoring port through which the first pull wire is threaded; and a second anchoring port through which the second pull wire is threaded. In a further example, a diameter of the drum is less than a diameter of the anchoring cylinder. In another example, a maximum outer diameter of the proximal end and the distal end of the endoscope is less than 6 mm.

In another aspect, the technology relates to a drive system housed within an endoscope. The drive system includes a first motor comprising a first axle; a first drum connected to the first axle such that rotation of the first axle causes rotation of the first drum, wherein the first drum comprises a first winding port to receive a first pull wire and a second winding port to receive a second pull wire; a first anchoring cylinder comprising a first anchoring port to receive the first pull wire and a second anchoring port to receive the second pull wire; a second motor positioned proximal from the first motor, comprising a second axle; a second drum connected to the second axle such that rotation of the second axle causes rotation of the second drum, wherein the first drum comprises a third winding port to receive a third pull wire and a fourth winding port to receive a fourth pull wire; and a second anchoring cylinder comprising a third anchoring port to receive the third pull wire and a fourth anchoring port to receive the fourth pull wire.

In an example, the first motor and the second motor have a maximum diameter of less than 6 mm. In another example, the drive system further includes an electrical interface coupled to electrical connections of the first motor and the second motor. In yet another example, rotation of the first drum in a first direction causes a steerable tip of the endoscope to bend in a first direction; rotation of the first drum in a second direction causes the steerable tip to bend in a second direction; rotation of the second drum in the first direction causes the steerable tip to bend in a third direction; and rotation of the second drum in the second direction causes the steerable tip to bend in a fourth direction.

BRIEF DESCRIPTION OF THE DRAWINGS

The following drawing figures, which form a part of this application, are illustrative of aspects of systems and methods described below and are not meant to limit the scope of the disclosure in any manner, which scope shall be based on the claims.

DETAILED DESCRIPTION

Figure 1:
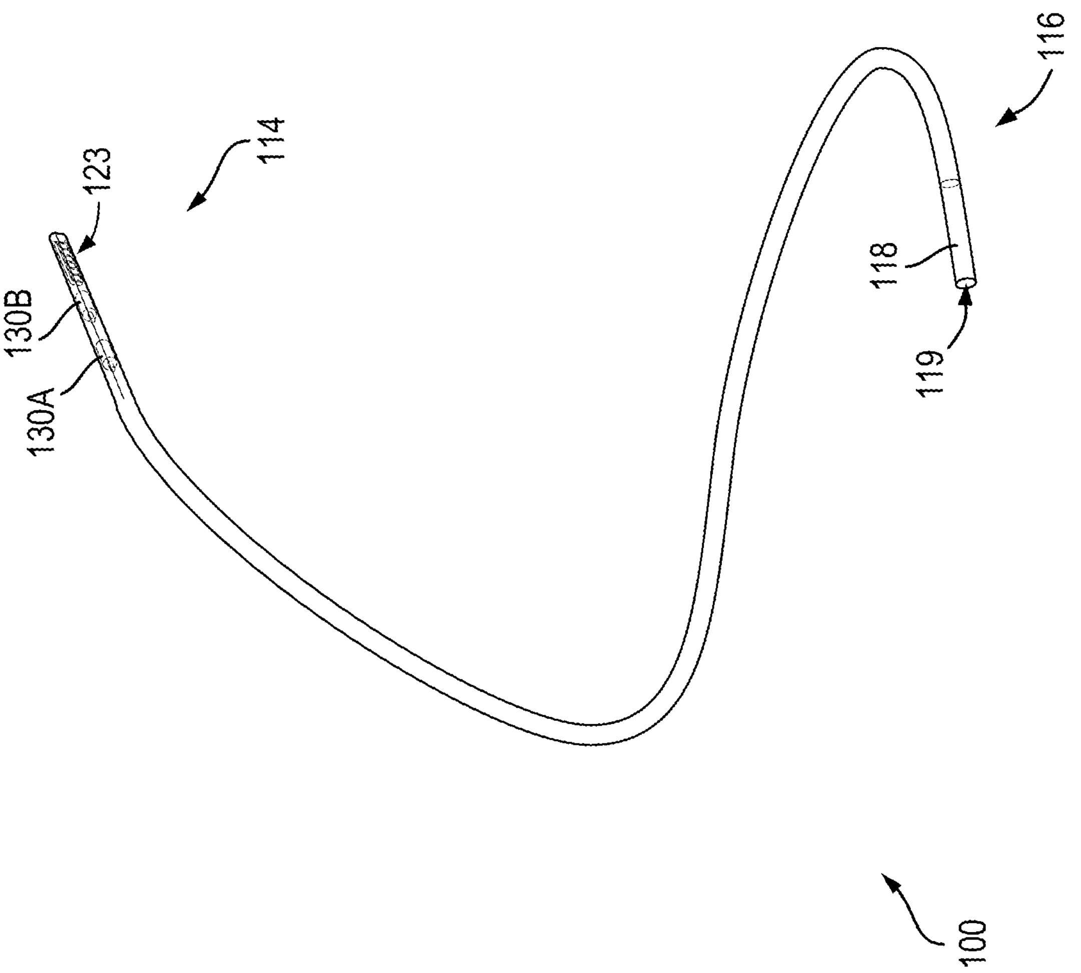
FIG. 1 depicts an example steerable endoscope.

Patients who require breathing assistance may be connected to a mechanical ventilator via breathing tube (e.g., an endotracheal tube). In a medical procedure referred to as an intubation, a clinician inserts a breathing tube into the mouth of the patient, past the larynx, and into the trachea. The breathing tube may then be connected to a ventilator or other device for supplying breathing gases to the patient. A laryngoscope may be used during intubation to help the clinician manipulate portions of the patient's anatomy, such as the tongue and epiglottis, and obtain a view of the larynx sufficient for inserting the breathing tube into the trachea. To further help visualize the larynx, some laryngoscopes may be configured with a video camera. A laryngoscope that includes a video camera may be referred to as a video laryngoscope (VL).

With some patients, performing an intubation may be difficult due to a variety of factors, such as inability to position the head or neck of the patient (e.g., due to injury), airway obstruction, atypical anatomy of the patient, other health considerations, or a combination of these or other factors. In these types of scenarios, clinicians may augment the use of a VL with a steerable endoscope, which is a narrow, flexible tube that typically includes its own video camera system integrated into a steerable distal tip that is inserted into the patient's body. The proximal end of the endoscope is removably connected to an external device capable of displaying video images from the endoscope camera and receiving control input from the user for controlling the steerable tip. In some examples, the endoscope may be connected to a VL designed to receive the endoscope and function both as a VL and as a display/control device for the endoscope. In other examples the endoscope may be connected to another type of control device designed to receive the endoscope.

During intubation, the endoscope may be navigated into the airway and positioned such that it provides supplemental visualization of the airway and facilitates insertion of the breathing tube. In some examples, the breathing tube is passed over the endoscope and into position in the airway, with the endoscope itself serving as a channel or guide for inserting the breathing tube. When the breathing tube is placed over the endoscope prior to inserting the endoscope into the patient's airway, the breathing tube is described as being "pre-loaded" onto the endoscope. When the breathing tube is placed over the endoscope after insertion, the breathing tube is described as being "post-loaded." An endoscope used as a guide for breathing tube insertion (either pre-loaded or post-loaded) may perform the same or similar functions as an introducer and may alternatively be referred to as an introducer in some examples.

Following insertion of the breathing tube, the endoscope may be removed from the breathing tube and/or airway, and ventilation of the patient may commence. While the VL may be cleaned for reuse, the endoscope may be designed for one-time-use, where the endoscope is treated as disposable and discarded after use in a single intubation. As such, the endoscope may be designed with reduced complexity and component count, in order to reduce the cost of the instrument. In an example design approach, steering forces may be generated by electric motors included in the VL and mechanically transmitted (such as by gears, shafts, etc.) to a drive system included in the endoscope. One disadvantage to this approach is that the mechanical elements that link the motors to the drive system may introduce mechanical slack or backlash, which may reduce steering control responsiveness. Another disadvantage is that when the endoscope is disconnected from the VL, such as to post-load a breathing tube, the motors are no longer connected to the drive system and cannot maintain the orientation of the steerable tip. Handling of the endoscope during post-loading may affect the orientation of the steerable tip. In examples where a clinician may wish to reconnect the endoscope following post-loading, such as to view the airway, the clinician may need to re-orient the steerable tip, in order to re-establish a view of the airway.

The present disclosure describes a drive system for a disposable endoscope that avoids the mechanical interface between the VL and endoscope. The drive system includes a pair of DC motors positioned serially within the endoscope proximal end and oriented with rotational axes aligned parallel with the long axis of the endoscope. A drum is connected to the axle or shaft of each motor and used to wind/unwind pull wires, which connect to the steerable tip and cause articulation of the steerable tip according to rotation of each motor axle. Control of the steerable tip is provided solely through an electrical interface, which provides power and control signals from the VL to the motors within the endoscope and may support additional features of the endoscope. The present disclosure also describes a magnetic field-based sensing system for determining the orientation of the steerable tip by measuring the orientation of each drum. Additional details are now provided by way of discussion of the included drawings.

FIG. 1 depicts an example steerable endoscope 100. The endoscope 100 includes a steerable tip 118 at the distal end 116. The steerable tip 118 includes accessories 119, which may be used during operation of the endoscope 100. For example, the accessories 119 may include instrument ports and/or a camera system (e.g., a video camera, lights, etc.) that captures endoscope image data (e.g., video images of the airway) during use. In some examples, the accessories 119 may further include sensors, such as an accelerometer, a gyroscope, or an inertial measurement unit (IMU), which provides measurement data associated with the acceleration, angular velocity, position, and/or other variables associated with the position/orientation/movement of the steerable tip 118.

The steerable tip 118 is controlled by a drive system, housed within proximal end of the endoscope 100, that includes a first motor 130A and second motor 130B located in the proximal end 114 of the endoscope 100. The motors 130A-B may each be a type of DC motor, such as a servo motor, stepper motor, brushed coreless motor, or other type of DC motor. In the example steerable endoscope 100, the motors 130A-B are configured with rotational axes oriented parallel to the long axis of the endoscope 100. In other examples, the rotational axes of the motors 130A-B may be oriented perpendicular to the long axis of the endoscope 100, or the motors 130A-B may be configured with an alternative orientation.

The rotational axle of the first motor 130A is connected to a first drum, and the rotational axle of the second motor 130B is connected to a second drum (the drums are depicted in greater detail in FIGS. 2 and 3). Each drum is further connected to separate pairs of pull wires, which are routed along the length of the endoscope and are connected to different points within the interior of the steerable tip 118, or other portion endoscope distal end 116. The distal ends of the pull wires are coupled to the steerable distal tip 518, end the proximal ends of the pull wires are coupled to the drive system. A first pair of pull wires is connected to the first drum such that rotation of the first drum in one direction increases tension on a first pull wire of the pair (such as by winding the first wire along the drum to shorten it) and releases tension on a second pull wire (such as by unwinding the second wire from the drum to lengthen it) in an opposing fashion. Rotation of the first drum in the opposite direction reverses the tension/winding, causing the first pull wire to lengthen and the second pull wire to shorten. Similarly, rotation of the second drum causes first and second pull wires of a second pull wire pair to shorten/lengthen, according to the direction of drum rotation.

As opposing wires of a pull wire pair are shortened/lengthened, the steerable tip 118 is caused to articulate within a movement plane. For example, the pull wires of the first pair may be connected to opposite sides of the interior of the steerable tip 118, such that shortening of one of the pull wires and lengthening of the other pull wire causes the steerable tip 118 to move in a first plane (e.g., left and right). The second pair of pull wires may be configured to cause movement of the steerable tip 118 in a second plane (e.g., up and down), that is substantially orthogonal to the first plane. Accordingly, three-dimensional movement (e.g., four-direction control) of the steerable tip 118 may be controlled by two motors via four pull wires. In some examples, movement of the steerable tip 118 may not be limited to rectilinear motion, and in further examples, the first and second movement planes may not be orthogonal to each other.

The drive system at the endoscope proximal end 114 may also include an electrical interface 123, which includes electrical contacts for receiving electrical power and transmitting/receiving signals to/from an external device, such as a VL. For example, the electrical interface 123 provides power and/or steering control signals from the VL to the motors 130A-B for controlling the movement of the endoscope steerable tip 118. The electrical interface 123 also provides a source of input power for operating the accessories 119 (such as sensors, cameras, light sources, and other elements described above), and/or other sensors or electronic elements included within the endoscope 100.

Further, the electrical interface 123 provides a data path for transmitting sensor data, video images, and/or other types of data from the endoscope 100 to the external device. For instance, video image data captured by the endoscope camera system may be transmitted to the external device via the electrical interface 123. In some examples, signals or data (such as clock, enable, timing, and/or other signals) may be transmitted through the electrical interface 123 in order to enable or configure operation of the steerable endoscope 100.

During use, the proximal end 114 of the endoscope 100 may be connected to the VL (or other external device) by a variety of methods. For example, the proximal end 114 may slide or be plugged into a connection port of the VL. When the endoscope is connected to the VL, conductive elements of the electrical interface 123 contact corresponding elements of the VL, allowing power to be provided by the VL, and enabling electrical signals to be transmitted/received between the endoscope 100 and VL. The conductive elements of the electrical interface 123 may include a plurality of conductive pads, receptacles, pins, balls, ports, and/or other conductive elements suitable for establishing electrical connection between the endoscope 100 and VL. An example of how the endoscope 100 may be connected to a VL is depicted in FIG. 5 and described below.

Figure 2A:
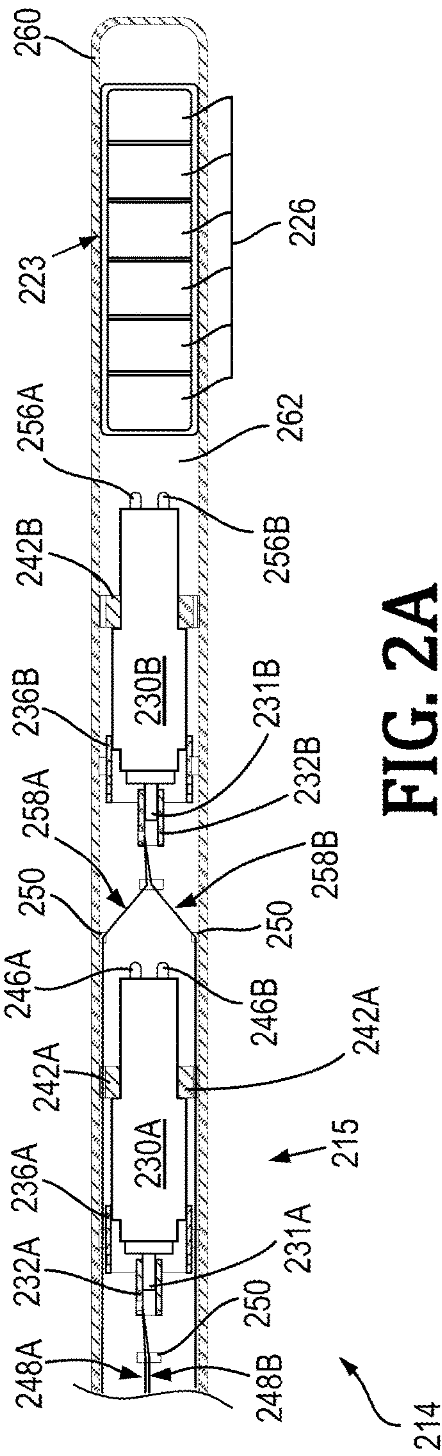
FIGS. 2A-2B are cross-sectional views of the proximal end of an example steerable endoscope.
Figure 2B:
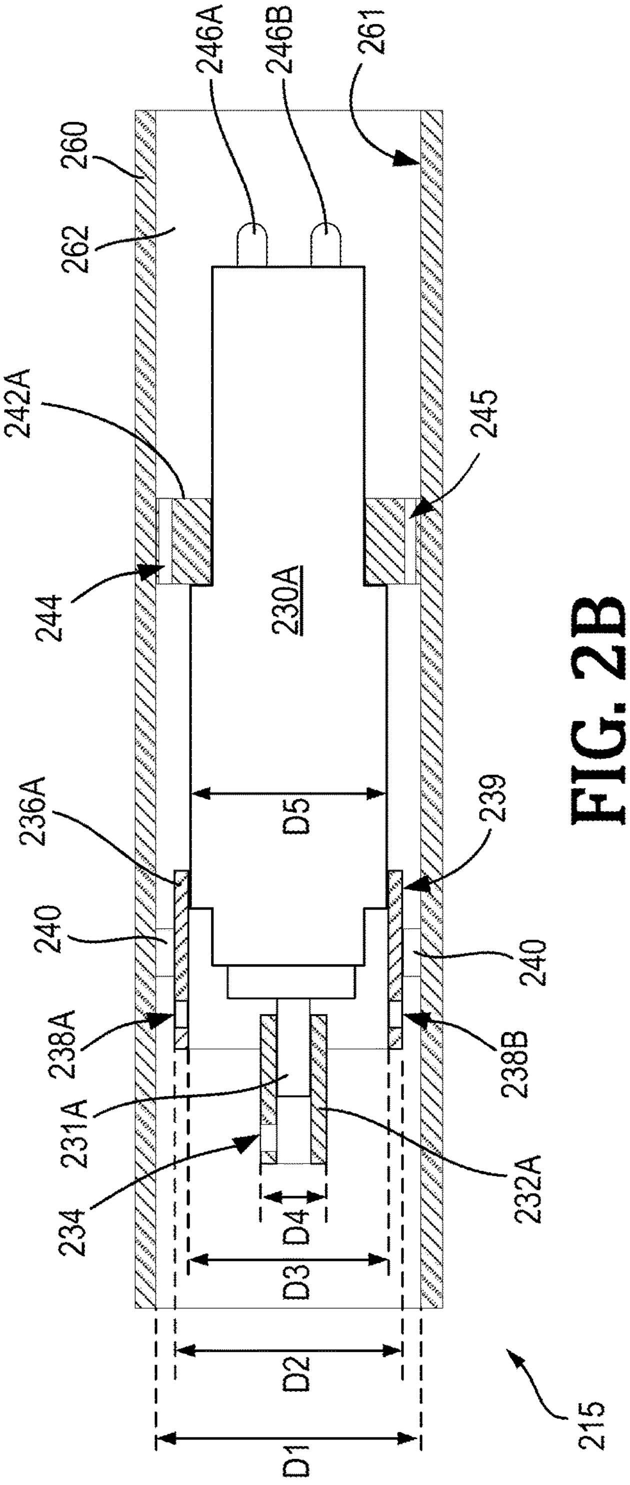

FIG. 2A is a side cross-sectional view of the proximal end 214 of an example steerable endoscope, and FIG. 2B is an enhanced side cross-sectional view of region 215 near the first motor 230A. The proximal end 214 includes features and/or elements that may be similar to, or the same as, features and/or elements described with respect to proximal end 114 of endoscope 100, depicted in FIG. 1. For example, the proximal end 214 includes a first motor 230A, a second motor 230B, and an electrical interface 223, which may function the same as motors 130A-B and electrical interface 123, respectively.

The first motor 230A includes a motor axle 231A connected to a drum 232A. The drum 232A may be secured to the motor axle 231A, such as by adhesive, welding (e.g., laser welding), or other mechanical method (e.g., a set screw), so that rotation of the motor axle 231A causes concurrent rotation of the drum 232A. A first pull wire 248A and second pull wire 248B are coupled to the drum 232A. For instance, the first pull wire 248A and second pull wire 248B may be threaded through a winding port 234 of the drum 232A and wound in opposite directions around the exterior of the drum 232A. The pull wires 248A-B may be metal, plastic, composite, or other type or combination of materials suitable for transmitting steering force from the motor 230A to the endoscope steerable tip.

The winding port 234 and other elements associated with the first motor 230A are more easily visualized in the enhanced view of region 215 presented in FIG. 2B. The pull wires 248A-B, however, have been excluded in FIG. 2B to aid visualization. The pull wires 248A-B are further threaded through anchoring ports 238A-B of the anchoring cylinder and affixed to the anchoring cylinder 236A, which remains static relative to the rotation of the drum 232A. With the ends of the pull wires 248A-B affixed to the anchoring cylinder 236A, rotation of the drum 232A in a first direction causes one of the pull wires (e.g., pull wire 248A) to wind onto the drum 232A (shorten) and the remaining pull wire (e.g., pull wire 248B) to unwind from the drum 232A (lengthen). FIGS. 3A-D, discussed in further detail below, depict one example of a method for threading, winding, and affixing pull wires 248A-B to a drum 232A and anchoring cylinder 236A.

Continuing with FIGS. 2A-B, the anchoring cylinder 236A may be affixed to the motor 230A and/or to a set of two or more spacers or mounts 240, which are themselves affixed to a portion of the interior surface of the outer jacket 260 of the endoscope. The mounts 240 may help align and secure the anchoring cylinder 236A and motor 230A within the endoscope lumen 262, while allowing other elements of the endoscope to be routed past the motor 230A. For example, the mounts 240 may provide one or more openings between the motor 230A and the outer jacket 260 for the passage of pull wires 258A-B associated with the second motor 230B (depicted in FIG. 2A). In some examples, the mounts 240 may be a part of the outer jacket 260, while in other examples the mounts 240 may be part of the anchoring cylinder 236A. In still other examples, the mounts 240 may be a single, annular spacer that surrounds the anchoring cylinder 236A and that provides one or more openings for the passage of pull wires 258A-B and/or other elements of the endoscope.

The proximal end 214 may also include another annular mount 242A that further secures and aligns motor 230A within the lumen 262 of the endoscope proximal end 214. The mount 242A may be integrated with and/or part of the outer jacket 260 and may be affixed to each motor 230A-B by any of a variety of methods (e.g., adhesive, laser welding, press fit, etc.). In some examples, the mount 242A may be a separate element, rather than being integrated with the outer jacket 260 and/or motor 230A.

The mount 242A may include two or more passthroughs 244, 245 that allow pull wires 258A-B, associated with the second motor 230B, to be routed past the first motor 230A, such as between the motor 230A and the outer jacket 260. In some examples, the mount 242A may include a single passthrough large enough to accommodate both pull wires 258A-B and/or other elements of the endoscope that are routed past the motor 230A. For instance, the mount 242A (and mounts 240) may provide for the passage of electrical wires or other electrical conductors that connect electrical elements at the distal end of the endoscope (e.g., a camera system, sensors, etc.) to the electrical interface 223.

In other examples, the mount 242A may include two or more discrete mounts, rather than a single annular mount 242A. For example, the mount 242A may be implemented as a set of two or more discrete mounts, similar to mounts 240, that are distributed at one or more locations along the length of the motor 230A, and/or circumferentially around the motor 230A.

As depicted in FIG. 2B, the lumen 262 has a diameter D1; the anchoring cylinder 236A has an outer diameter D2 and an inner diameter D3; the drum 232A has an outer diameter D4; and the motor 230A has an outer (largest) diameter D5. The diameter D1 may be relatively small, such as less than 7 millimeters (mm), 6 mm, 5 mm, or 4 mm. In some examples, the maximum diameter of the endoscope remains substantially consistent throughout the length of the endoscope. For instance, outer diameter of the proximal end and the outer diameter of the distal end may both be less than 7 mm, 6 mm, 5 mm, or 4 mm. Accordingly, the entire endoscope may be passed through small passageways, such as through an endotracheal tube.

The drum diameter D4 of the drum 232A may be selected to achieve a specific winding/unwinding rate of the pull wires 248A-B. For instance, a larger drum diameter D4 may result in greater portions of the pull wires 248A-B being wound/unwound per rotation of the drum 232A. However, a larger drum diameter D4 may require a motor 230A that has the ability to apply greater torque, which may necessitate a larger motor 230A, such as a motor 230A with a larger diameter D5. In some examples, the drum diameter D4 may be chosen to provide full range of motion of the endoscope steerable tip with a total rotation of the drum 232A of no more than 360°. A detailed example is described further below with respect to FIGS. 4A-C.

In addition, the anchoring cylinder 236A may have an outer diameter D2 that is substantially equal to the lumen diameter D1, where the cylinder outer surface 239 of the anchoring cylinder 236A may contact the jacket inner surface 261. In such examples, mounts 240 may be excluded, and/or the anchoring cylinder 236A may include one or more passthrough features that allow pull wires 258A-B associated with the second motor 230B, and other elements of the endoscope, to be routed past the motor 230A and anchoring cylinder 236A. In examples, the anchoring cylinder 236A may be integrated with, or part of, the outer jacket 260, and may provide features for threading and/or affixing pull wires 248A-B.

While the anchoring cylinder inner diameter D3 is depicted in FIGS. 2A-B as being substantially equal to motor outer diameter D5, in examples the inner diameter D3 and outer diameter D5 may not be substantially equal. For instance, the anchoring cylinder 236A may contact the motor 230A at a different (smaller) portion of the motor 230A or may not make direct contact with the motor 230A at all. As such, the diameter D3 may not be associated with any dimensions of the motor 230A.

In some examples, the motor outer diameter D5 may be substantially equal to the jacket inner diameter D1, such that portions of the motor 230A contact the jacket inner surface 261. In such an example, the mount 242A may not be included, and the motor 230A may be secured to the jacket inner surface 261 by any of a variety of methods, such as by adhesive, laser welding, press fit, etc.

In examples, motor 230B and elements associated with motor 230B, such as pull wires 258A-B, motor axle 231B, drum 232B, anchoring cylinder 236B, mounts 242B, etc., may be similar to, or the same as, motor 230A and corresponding elements associated with motor 230A. In other examples, motor 230B and/or elements associated with motor 230B may be different than motor 230A and/or elements associated with motor 230A. For instance, motor 230B may be associated with mount 242B that is shaped differently than mount 242A, and/or mount 242B may have different dimensions than mount 242A and/or a different configuration of passthrough elements. Similarly, drum 232B and/or anchoring cylinder 236B may have different diameters and/or shapes than drum 232A and anchoring cylinder 236A, respectively. In addition, the motors 230A-B, drums 232A-B, anchoring cylinders 236A-B, and other elements of the proximal end 214 are depicted in FIGS. 2A-B and described as being cylinders or cylindrically shaped. In some examples, elements depicted and/or described as being cylinders or cylindrically shaped may be designed with other shapes, dimensions, and/or form factors.

FIGS. 2A-B also depict a set of guides 250 associated with the routing of pull wires 248A-B, 258A-B. For instance, the guides 250 may provide a method for directing pull wires 258A-B to the periphery of the lumen 262, so that the pull wires 258A-B may be routed past the motor 230A. The guides 250 may further prevent the pull wires 248A-B, 258A-B from interfering with each other, or otherwise becoming impinged or entangled. The guides 250 may include one or more rings, eyelets, hooks, and/or other elements or features that direct the pull wires 248A-B, 258A-B. In examples, the guides 250 may be low-friction or may be designed to reduce friction between the pull wires 248A-B, 258A-B and contact surfaces of the guides 250.

In another example, rather than including one or more of the anchoring cylinders 236A-B, spacers 240, mounts 242A-B, and/or guides 250, each of the motors 230A-B and corresponding pull wires 248A-B and 258A-B may be secured within the outer jacket 260 by a framing system. Each framing system may include a set of rigid rods or other rigid framing members spaced circumferentially around each of the motors 230A-B, which may be affixed to each framing system by any variety of methods, such as adhesive, laser welding, or other method. Each framing system may also be used to guide, route, and/or secure portions of the pull wires 248A-B and 258A-B.

Further, each of the framing systems may be spaced apart from one another longitudinally, in order to provide a flexible region between the motors 230A-B. In one example, the first motor 230A may be secured to the outer jacket 260 by a first framing system, that includes a set of two or more rods that are longer than the first motor 230A, and that are spaced circumferentially around the first motor 230A. The second motor 230B may be secured to the outer jacket 260 by a second framing system that may be similar to, or the same as, the first framing system. The first and second framing systems may be separated longitudinally by a distance suitable for providing a flexible region between the framing systems, which may facilitate the process of guiding a breathing tube over the endoscope proximal end 214 (such as during pre- or post-loading). For example, the first and second framing systems (rigid sections) may each be less than 45 mm long, or in some examples may be less than 40 mm long and may be spaced apart by 20 mm or less (to form a flexible section therebetween), or in some examples may be spaced apart by 15 mm or less. In some examples, the ratio of the rigid framing system sections to the flexible region between the framing systems may be 3:1, where the length of the rigid framing system sections are each approximately three times longer than that of the flexible region. In other examples, the ratio of length of the rigid sections to the length of the flexible region may be a larger or smaller ratio.

The endoscope proximal 214 end also includes electrical interface 223 that further includes a plurality of electrical contacts 226. In examples, the electrical contacts 226 may be any type of conductive element, such as pads, receptacles, pins, balls, ports, and/or other conductive elements suitable for establishing electrical connection to corresponding elements of an external device, such as a VL (depicted in FIG. 5). Connections between the electrical contacts 226 and electrical elements of the endoscope may be provided by wire, printed circuit board (PCB), flexible printed circuit (flex), and/or other connection methods, which are not depicted for visual clarity.

When the endoscope proximal end 214 is connected to an external device (e.g., the VL), the electrical interface 223 provides power to electrical elements of the endoscope and is used to transmit/receive electrical signals between elements of the endoscope and the VL. For example, one or more of the electrical contacts 226 may provide electrical power and control signals to the motor electrical connections 246A-B and 256A-B for control of the endoscope steerable tip. In some examples, motors 230A-B may include additional input electrical connections, such as three or more total electrical connections for each of the motors 230A-B.

Further, one or more electrical contacts 226 may supply power to other electrical elements of the endoscope, such as the endoscope camera system, any sensors that may be present in the endoscope (e.g., IMU, accelerometer, etc.), and/or other electrical elements. One or more electrical contacts 226 may be used to transmit video images from the endoscope camera system to the VL, while other electrical contacts 226 may be used to transmit other types of data (such as sensor data) to the VL. In some examples, the one or more electrical contacts 226 may be used for transmitting/receiving other types of signals, such as clock, timing, enable, and/or other types of signals used for the operation of the endoscope. For instance, one or more electrical contacts 226 may be used for transmitting/receiving signals between the VL and other electrical elements included in the endoscope, such as processors, memory, and/or other types of circuit elements.

FIGS. 3A-3D depict an example winding system for connecting a pair of pull wires 348A-B to an example drum 332 and anchoring cylinder 336. The drum 332, anchoring cylinder 336, and pull wires 348A-B may be similar to, or the same as, the drum 232A-B, anchoring cylinders 236A-B, and pull wires 248A-B, 258A-B described above with respect to FIG. 2A-B.

Figures 3A, 3B, 3C, 3D:
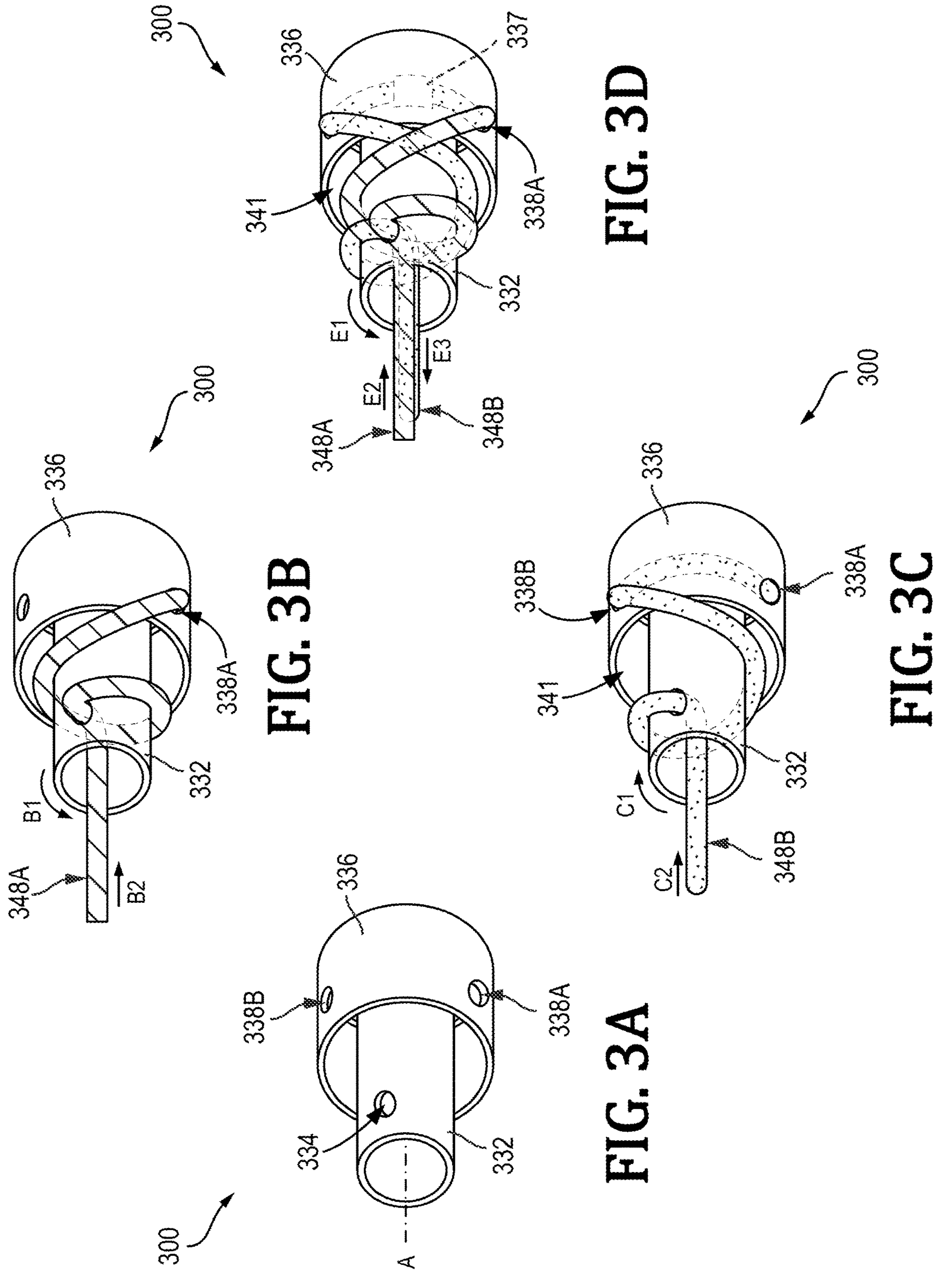
FIGS. 3A-3D depict views of an example winding system.

FIG. 3A depicts an example winding system 300 with pull wires 348A-B excluded for better visualization. The drum 332 may be a fully or partially hollow cylinder that is affixed to the axle of a motor, such as depicted in FIG. 2B. Rotation of the motor axle causes concurrent rotation of the drum 332 about axis A. Pull wires 348A-B are threaded through a winding port 334 of the drum 332. The winding port 334 helps the drum 332 apply rotational force from the motor axle to the pull wires 348A-B. In other examples, the winding port 334 may be a notch, post, guide, or other type of element suitable for applying rotational force to the pull wires 348A-B.

The anchoring cylinder 336 is positioned substantially coaxial with the drum 332. The anchoring cylinder 336 may be affixed to a non-rotational portion of the motor or may be affixed to another stationary element of the steerable endoscope, such that the anchoring cylinder 336 remains stationary relative to the drum 332. The anchoring cylinder 336 includes at least two anchoring ports 338A-B through which the pull wires 348A-B are threaded.

FIG. 3B depicts the example winding system 300 in which the first pull wire 348A is shown and the second pull wire 348B is not shown for better visualization. In the depicted example, the first pull wire 348A is threaded through the winding port 334 and wound in a first direction (e.g., clockwise) around the drum 332. The first pull wire 348A is further threaded through the first anchoring port 338A and affixed within the anchoring cylinder 336 (described below), such that the end of the first pull wire 348A is held in position within the anchoring cylinder 336. When the drum 332 is rotated in a counterclockwise direction, as indicated by arrow B1, the drum 332 applies tension to the first pull wire 348A, causing the first pull wire 348A to be drawn toward the drum 332, as indicated by arrow B2. As the first pull wire 348A is drawn toward the drum 332, the first pull wire 348A is pulled through the winding port 334 and wound onto the drum 332.

FIG. 3C depicts the example winding system 300 in which the second pull wire 348B is shown and the first pull wire 348A is not shown for better visualization. The second pull wire 348B is also threaded through the winding port 334, but unlike the first pull wire 348A, the second pull wire 348B is wound counterclockwise around the drum 332. The second pull wire 348B is further threaded through the second anchoring port 338B and routed along the interior surface 341 of the anchoring cylinder 336 to the first anchoring port 338A, where it may connect to the first pull wire 348A (described below). As the drum 332 is rotated in a clockwise direction, as indicated by arrow C1, the drum 332 applies tension to the second pull wire 348B, causing the second pull wire 348B to be drawn toward the drum 332, as indicated by arrow C2. As the second pull wire 348B is drawn toward the drum 332, the second pull wire 348B is pulled through the winding port 334 and wound onto the drum 332.

FIG. 3D depicts the example winding system 300 in which both pull wires 348A-B are shown. As described above with respect to FIG. 1, at the distal end of the steerable endoscope, the pull wires 348A-B are connected to interior portions of the steerable tip, such as to opposite interior sides of the steerable tip. Rotation of the drum 332 causes one of the pull wires (e.g., pull wire 348A) to shorten and allows the other pull wire (e.g., pull wire 348B) to lengthen, resulting in articulation of the steerable tip within a movement plane in the direction of the pull wire (e.g., pull wire 348A) that was shortened. For instance, the pull wires 348A-B may be connected to the interior of the steerable tip to cause movement of the steerable tip in a "left/right" movement plane. As one example, shortening of the first pull wire 348A and lengthening of the second pull wire 348B may cause the steerable tip to bend left, and shortening of the second pull wire 348B and lengthening of the first pull wire 348A may cause the steerable tip to bend right.

FIG. 3D illustrates the effect of counterclockwise rotation of the drum 332. Rotation of the drum 332, as indicated by arrow E1, causes the drum 332 to apply tension to the first pull wire 348A and release tension from the second pull wire 348B. The first pull wire 348A is drawn toward the drum 332, as indicated by arrow E2, and wound onto the drum 332 (thereby shortening the first pull wire 348A). The endoscope steerable tip is caused to bend in the direction of the first pull wire 348A (e.g., left). Simultaneously, the release of tension on the second pull wire 348B, and the movement of the steerable tip in the direction of the first pull wire 348A (left), allows the second pull wire 348B to be pulled away from the drum 332, as indicated by arrow E3, and unwound from the drum 332 (thereby lengthening the second pull wire 348B). Reversing the direction of rotation of the drum 332 (e.g., clockwise rotation) causes the opposite effect, where the endoscope steerable tip bends in the direction of the second pull wire 348B (e.g., right).

In addition, as depicted in FIG. 3D, the pull wires 348A-B may be connected within the anchoring cylinder 336. For example, the ends of the pull wires 348A-B may be tied, crimped, or otherwise connected together. In one example, the pull wires 348A-B may be a single continuous pull wire that is wound and threaded as shown, in order to create the effect of two opposing pull wires 348A-B. To help keep the pull wires 348A-B stationary, a section may be affixed to the cylinder inner surface 341, such as by adhesive 337, or by another fixation method.

In other examples, the pull wires 348A-B may be two or more discrete wires that may or may not be connected together. For instance, the pull wires 348A-B may be implemented as two distinct elements that are separately fixated within the anchoring cylinder 336, such as by multiple sections of adhesive 337 or other anchoring mechanism.

As depicted in FIG. 3D, the example winding system 300 is shown in a starting or "neutral" orientation, prior to rotation of the drum 332 in a counterclockwise direction. In this orientation, the endoscope steerable tip may also be in a starting or neutral orientation, such as where the steerable tip is straight (e.g., in a left/right movement plane), rather than bent or articulated. In other examples, a different neutral orientation may be defined for the drum 332 and/or the endoscope steerable tip.

Figures 4A, 4B, 4C:
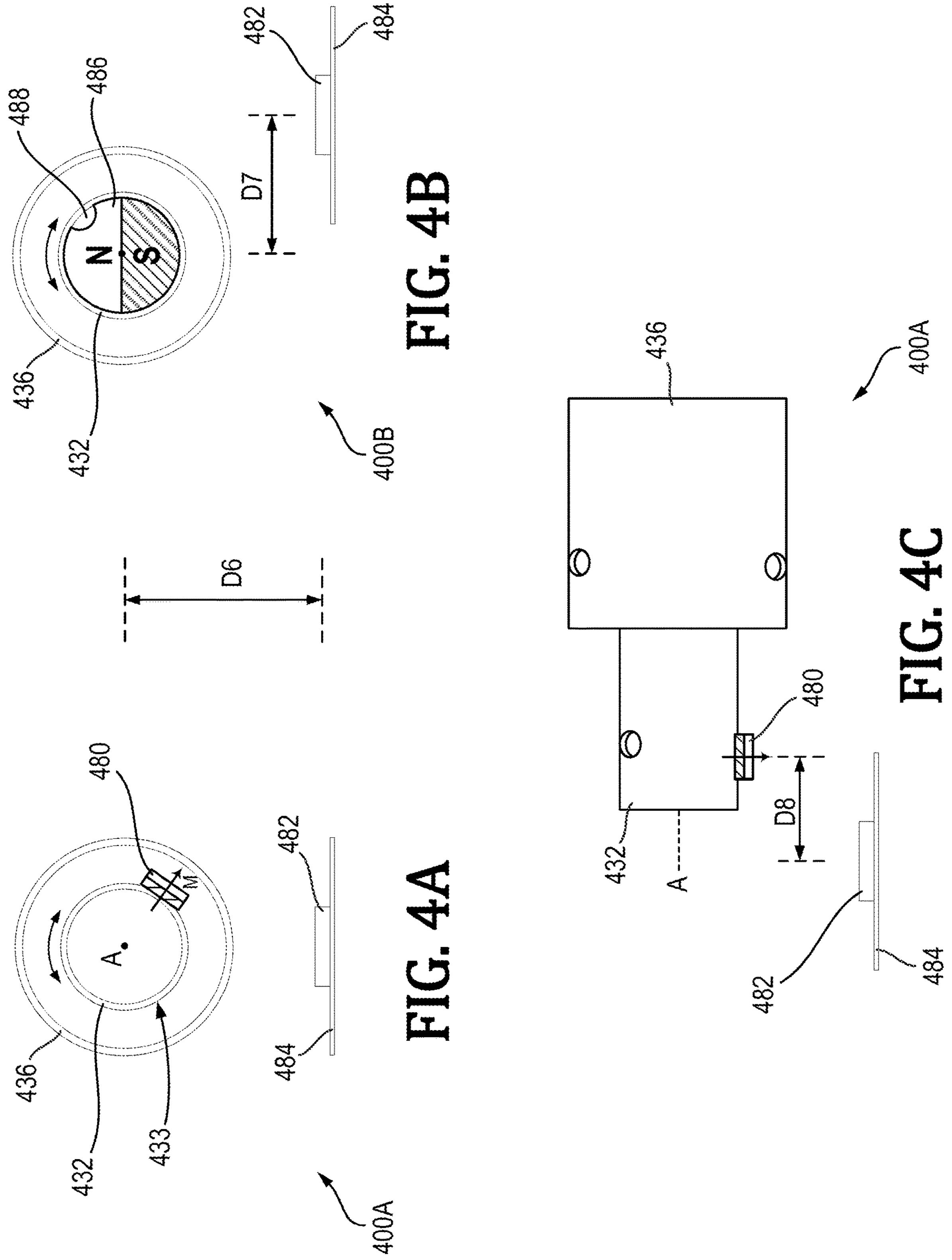
FIG. 4A depicts an example system for determining drum orientation.
FIG. 4B depicts another example system for determining drum orientation.
FIG. 4C is a side view of an example system for determining drum orientation.

FIG. 4A depicts a front (coaxial) view of an example system 400A for determining the orientation of the drum 432 using magnetic field sensing. The drum 432 and anchoring cylinder 436 may be similar to, or the same as, drums 232A-B, 332 and anchoring cylinders 236A-B, 336, respectively. As described above, the drum 432 is connected to, and rotates with, the axle of a motor (such as motor axle 231A in FIG. 2A-B), while the anchoring cylinder 436 remains stationary. The anchoring cylinder 436 may be connected to a stationary portion of the motor, the outer jacket of the endoscope, or some other non-rotating element of the endoscope.

The drum 432 includes a permanent magnet 480 which may be embedded in the wall of the drum 432 or may be attached to the outer surface 433 of the drum 432. The magnet 480 may be of any size and shape that can be accommodated by the drum 432 and may have a North-South (N-S) orientation suitable for establishing a magnetic field detectable by the magnetic field sensor 482. FIG. 4A depicts one example in which the N-S orientation of the magnet 480 is directed radially from the drum outer surface 433, as indicated by the arrow M. In other examples, the magnet 480 may have a different, size, shape, and/or N-S orientation.

The magnetic field sensor 482 may be any type of sensor capable of measuring the magnetic field produced by the magnet 480. For example, the sensor 482 may be a multi-axis Hall effect sensor, and at least one sensor 482 may be included for each motor in the steerable endoscope. The sensor 482 may be mounted to a circuit board 484, such as a rigid PCB, flex, or other type of circuit board. The circuit board 484 allows the sensor 482 to receive electrical power and to send/receive signals associated with the operation of the sensor 482. For instance, the circuit board 484 may be electrically connected to additional circuit elements (not depicted), such as a power source (e.g., a battery or power regulation circuit) and a processor or other element capable of communicating with the sensor 482 and receiving magnetic field measurement data. In examples, the circuit board 484 may be connected to electrical elements of the VL (or other external control device) through an electrical interface of the endoscope (such as electrical interface 223).

During operation, the drum 432 rotates clockwise/clockwise according to steering signals received by the motor to which the drum 432 is connected. The magnet 480 is rotated accordingly, which changes the direction and magnitude of the magnetic field measured at the sensor 482. Multi-axis magnetic field data measured by the sensor 482 may be used to calculate the orientation of the magnet 480, which indicates the amount of rotation of the drum 432. Further, the orientation of the drum 432 may be correlated with the orientation of the endoscope steerable tip. As an example, measured magnetic field data may indicate that the drum 432 is rotated 90° clockwise, which corresponds to a 45° bend in the steerable tip to the right, in a left-right movement plane. As another example, the measured magnetic field data may indicate that the drum 432 is rotated 180° counterclockwise, which corresponds to a 90° bend in the steerable tip to the left. Thus, the measured magnetic field data may be used to determine absolute orientation of the steerable tip.

In examples, the diameter of the drum 432 (e.g., diameter D4 of FIG. 2B) may be chosen so that the full range of motion of the steerable tip is achieved by no more than 360° of total rotation of the drum 432. For example, the endoscope may be designed so that the full range of motion of the steerable tip in a left-right movement plane is 90° to the left at one end of the range, 0° at a middle (neutral) point of the range, and 90° to the right at the other end of the range. The diameter of the drum 432 may be selected so that a 180° counterclockwise rotation of the drum 432 sufficiently winds/unwinds the pull wires to cause a maximum (90°) left bend, and a 180° clockwise rotation of the drum 432 sufficiently winds/unwinds the pull wires to cause a maximum (90°) right bend. In other examples, the diameter of the drum 432 may be selected to achieve a particular range of motion of the steerable tip greater than or less than 90° left/right for a 180° counterclockwise/clockwise rotation of the drum 432. In this regard, every orientation of the magnet 480 produces a unique magnetic field measurement at the sensor 482 for determining absolute orientation of the steerable tip.

In examples where the total rotation of the drum 432 exceeds 360° (e.g., clockwise and counterclockwise rotations of drum 432 exceed) 180°, portions of clockwise and counterclockwise rotations of the drum 432 may overlap, producing non-unique magnetic fields at the sensor 482. Thus, measured magnetic field data alone may not be sufficient for discerning the orientation of the steerable tip, such as discerning maximum left bends from maximum right bends. In such cases, the number of rotations or revolutions may be tracked or recorded (e.g., using memory elements included in the VL and/or steerable endoscope).

FIG. 4B depicts a front (coaxial) view of an example system 400B in which a larger magnet 486 may be included in the drum 432. The larger magnet 486 may produce a magnetic field with a higher magnitude, which may facilitate sensing of the magnetic field by sensor 482. The larger magnet 486 may occupy a significant portion, or the entirety, of the interior of the drum 432 and may be any of a variety of possible shapes and sizes. In examples where the larger magnet 486 significantly fills the interior of the drum 432, the larger magnet 486 may include a recess 488 for threading pull wires. The N-S orientation of the larger magnet 486 may also be directed radially from the center of the drum 432, similar to the magnet 480.

In example systems 400A and 400B the magnet 480 and larger magnet 486 are included as part of the drum 432. In other examples, a magnet may alternatively be included in other elements of the steerable endoscope. For example, a magnet may be included as part of the axle of each motor, rather than in the drum 432, or may be included in another rotational element associated with each motor.

As depicted in FIGS. 4A-4B, the sensor 482 may be located a distance D6 from the center of rotation A of the drum 432. In some examples, the proximal end of the steerable endoscope may accommodate the sensor 482 and circuit board 484 within the endoscope itself. In such examples, where the distance D6 is small, a smaller magnet (such as magnet 480) may be sufficiently sensed by the sensor 482. In other examples, the sensor 482 and circuit board 484 may be located in the VL (discussed below with respect to FIG. 5) or other external device or may otherwise be located at a larger distance D6. In these examples, a larger magnet (such as large magnet 486) may be selected to facilitate sensing of the corresponding magnetic field by sensor 482.

In addition, the sensor 482 and circuit board 484 may be located laterally from the center of rotation A of the drum 432. For example, the sensor 482 may be located a distance D7 from the center of rotation (e.g., offset left or right), in addition to distance D6. FIG. 4C further depicts a side view of example system 400A, in which the sensor 482 and circuit board 484 are located distally from the magnet 480 by a distance D8. In some examples, the sensor 482 and circuit board 484 may be located proximally from the magnet 480 by a distance D8.

FIG. 5 depicts an example video system 500, which includes a video laryngoscope (VL) 502 capable of connecting to and controlling a steerable endoscope 506. The endoscope 506 may be similar to, or the same as, endoscope 100, described above with respect to FIG. 1. The endoscope proximal end 514 includes two motors 530A-B and an electrical interface 523A. The endoscope distal end 516 includes a steerable tip 518 and accessories 519 (such as a camera system, sensors, etc.). The motors 530A-B are connected to drums (depicted in FIG. 2A-B), which are further connected to pull wires that are routed down the length of endoscope 506 and connected to the steerable tip 518. The motors 530A-B receive power and/or electrical control signals through the electrical interface 523A and rotate the drums to cause bending of the steerable tip 518 as described herein.

The endoscope 506 is connected to the VL 502 via detachable cartridge 504. The endoscope proximal end 514 slides into the cartridge guide 520, where elements of the endoscope electrical interface 523A make electrical contact with corresponding elements of cartridge electrical interface 523B. The cartridge 504 is further connected to the VL rear surface 503, where elements of the cartridge 504 and/or VL 502 cause the cartridge 504 to be retained against the VL rear surface 503. For example, magnetic elements (not depicted) may be included in the cartridge 504 and/or the VL 502 and may apply force to hold the cartridge 504 to the VL rear surface 503.

Figure 5B:
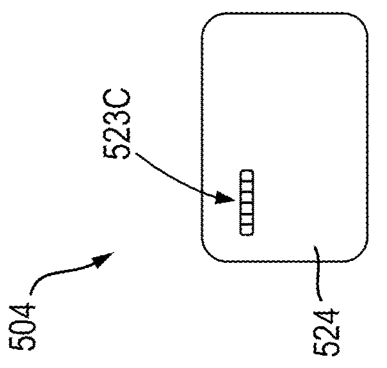
FIGS. 5A-5B depict an example video system that includes a steerable endoscope.
Figure 5A:
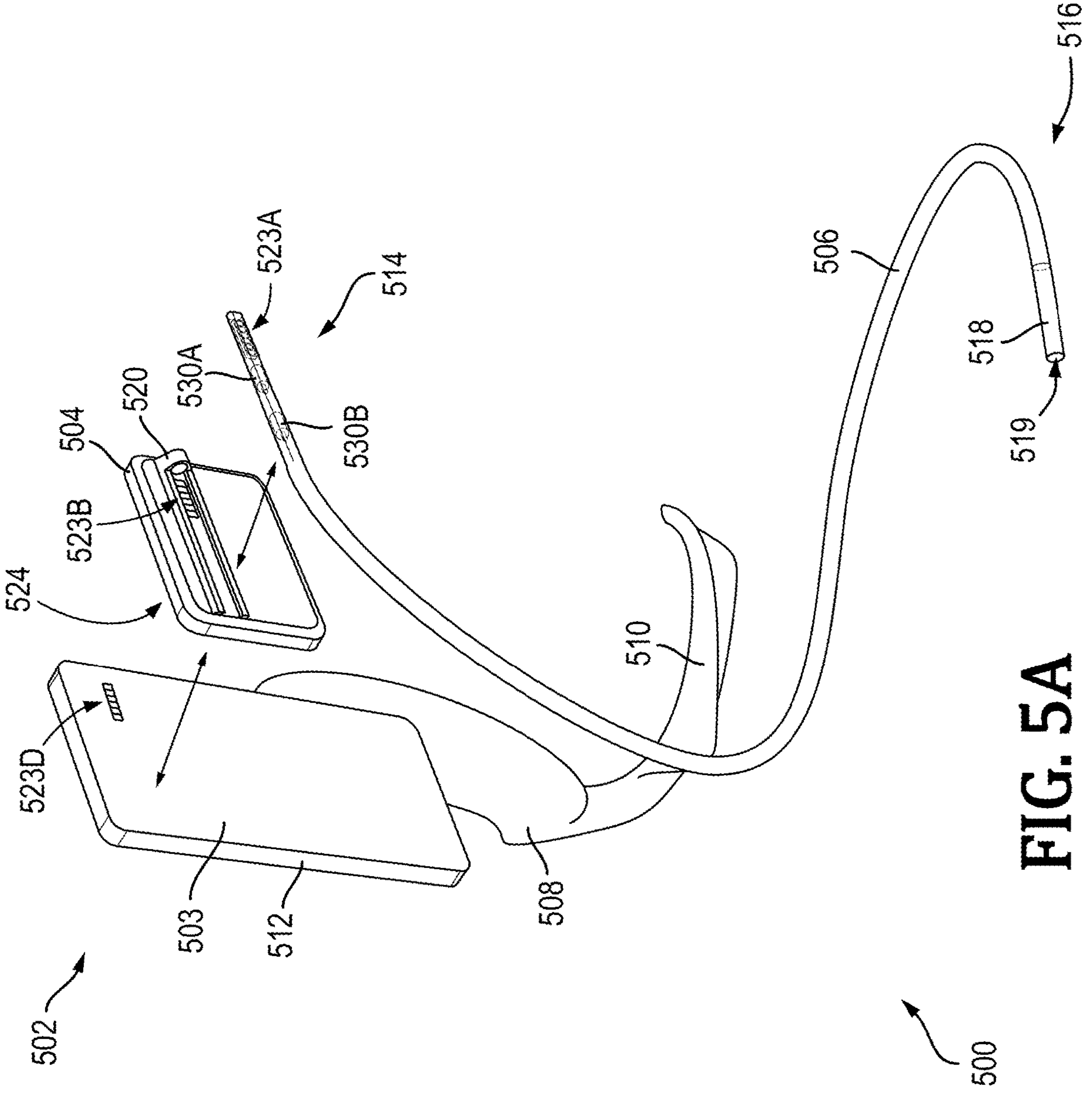

As depicted in FIG. 5B, the cartridge rear surface 524 includes an electrical interface 523C that makes electrical contact with VL electrical interface 523D when the cartridge 504 is connected to the VL 502. The cartridge electrical interfaces 523B-C may be connected within the cartridge 504 by any of a variety of connection methods, such as by electrical wire, rigid or flexible pins, PCB, flex, and/or other methods of electrical connection. The electrical interfaces 523B-C may include additional electrical elements, such as active and/or passive circuit components.

The VL electrical interface 523D is connected to electrical elements within the VL 502 for supporting operation of the endoscope 506. For example, the VL electrical interface 523D is connected to power supply elements (e.g., a battery, power regulation circuitry, etc.), control elements for controlling motors 530A-B, digital processing elements (e.g., a processor) for processing and/or analyzing sensor and camera image data, and/or other analog and digital circuit elements that support the operation of the endoscope 506.

The VL 502 also includes a display 512, handle 508, and extension 510 (which may alternatively be referred to as a blade). The extension 510 may include a VL camera system (e.g., a video camera, lights, etc.), or may include optical features or elements that support a VL camera system located in another part of the VL 502. The display 512 may be used to display data acquired by any of the sensors associated with the example video system 500, and to display images acquired by the VL camera system and/or the endoscope camera system. For example, the display 512 may be capable of switching between the two camera systems during operation, so that a clinician may select a preferred viewpoint. In some examples, the display 512 may be capable of displaying images from both camera systems simultaneously, such as by split screen, picture-in-picture, or other display methods.

The display 512 may be any of a variety of display technologies, such as LCD, LED, OLED, or other display technology. In examples, the display 512 may be a touch-sensitive display (e.g., a capacitive touch-sensitive display) that allows user input to be received through the display 512. Further, the display 512 may receive steering inputs from a user of the VL 502 for control of the endoscope steerable tip 518, or in some examples, the user may provide steering inputs via input keys or buttons associated with the VL 502.

Elements of the VL 502 (such as a processor and/or other elements) may translate the received control inputs into corresponding motor control signals, which are transmitted to the motors 530A-B through the cartridge 504 (via electrical interfaces 523A-D) for control of the steerable tip 518.

Components of the example video system 500 may also include two or more Hall effect sensors for determining the orientation of drums associated with motors 530A-B. As described with respect to FIG. 4, the drums, motor axles, or other rotational elements of the motors 530A-B may each include a permanent magnet whose orientation may represent the orientation of the steerable tip 518. In some examples, the Hall effect sensors (not depicted in FIGS. 5A-B) may be included in the endoscope proximal end 514 and may provide measured magnetic field data to the VL 502 through the electrical interfaces 523A-D. The data may be processed by elements of the VL 502 (such as by a processor) to determine drum orientation, from which the orientation of the steerable tip 518 may be determined. The VL 502 may display data related to the orientation of the steerable tip 518 on the display 512.

Alternatively, the detachable cartridge 504 or VL 502 may include Hall effect sensors, where the sensors may be located within the cartridge 504 or VL 502 near enough to the motors 530A-B to effectively sense the orientation of each permanent magnet. Including the Hall effect sensors in the VL 502 may reduce the complexity, component count, and cost of the cartridge 504 and/or endoscope 506 and may allow the cartridge 504 and/or endoscope 506 to be treated as one-time-use or disposable.

In still other examples, the endoscope 506 may include an additional permanent magnet not associated with rotational elements of the motors 530A-B. For instance, the additional magnet may be affixed to another portion of the interior of the endoscope proximal end 514, such that the additional magnet remains static relative to rotational elements associated with the motors 530A-B. The detachable cartridge 504 or VL 502 may include a dedicated sensor (such as an additional multi-axis Hall effect sensor) for determining the orientation of the additional magnet, which further indicates the orientation of the endoscope proximal end 514. In one example, the orientation of permanent magnets associated with rotational elements of the motors 530A-B may be compared to the orientation of the additional (fixed) permanent magnet to determine the absolute orientation of each motor shaft or drum. This approach may enable connection between an endoscope 506 and a VL 502 or cartridge 504 that is agnostic to the orientation of the endoscope 506. For example, the endoscope 506 may be designed with multiple sets of electrical contacts, such that the proximal end 514 may be connected to the VL 502 or cartridge 504 in more than one orientation.

During intubation, the extension 510 is inserted into the airway of the patient and used to manipulate the anatomy of the patient for breathing tube insertion. The endoscope distal end 516 may also be inserted into the patient's airway to augment the view provided by the VL 502. Steering commands may be provided by the clinician (such as through display 512) to cause articulation of the steerable tip 518, which may allow the endoscope camera to provide an improved view of the airway to facilitate the intubation.

In addition, during operation, the endoscope 506 may be removed from the detachable cartridge 504 so that a clinician may post-load a breathing tube. Handling of the endoscope 506 during post-loading may result in a change in the orientation of the steerable tip 518. In examples where the endoscope proximal end 514 is reconnected to the cartridge 504 following post-loading, Hall sensor data may be used by the VL 502 to reconfigure steering control to compensate for any changes in orientation of the steerable tip 518. Additionally, or alternatively, the VL 502 may alert the clinician to the new orientation, such as by providing a visual alert on the display 512 or by providing another kind of indication or alert. The VL 502 may also display information associated with the orientation of the steerable tip 518 on the display 512, such as by displaying the new orientation, the change in orientation, and/or by displaying other types of information.

In other examples, the steerable endoscope 506 may be connected to other types of devices capable of interfacing with the endoscope 506 and controlling the steerable tip 518. For example, some types of VLs 502 may allow for direct connection of the endoscope 506, without a detachable cartridge 504. In other examples, other types of devices, such as a dedicated endoscope controller, may allow connection of the endoscope 506 and may provide steering control of the steerable tip 518.

While the above description primarily refers to endoscopes, the present technology may also be applied to and incorporated into other types of elongate medical instruments, such as catheters or introducers. Those skilled in the art will recognize that the methods and systems of the present disclosure may be implemented in many manners and as such are not to be limited by the foregoing aspects and examples. In other words, functional elements being performed by a single or multiple components. In this regard, any number of the features of the different aspects described herein may be combined into single or multiple aspects, and alternate aspects having fewer than or more than all of the features herein described are possible. Functionality may also be, in whole or in part, distributed among multiple components, in manners now known or to become known.

Further, as used herein and in the claims, the phrase "at least one of element A, element B, or element C" is intended to convey any of: element A, element B, element C, elements A and B, elements A and C, elements B and C, and elements A, B, and C. In addition, one having skill in the art will understand the degree to which terms such as "about" or "substantially" convey in light of the measurement techniques utilized herein. To the extent such terms may not be clearly defined or understood by one having skill in the art, the term "about" shall mean plus or minus ten percent.

Numerous other changes may be made which will readily suggest themselves to those skilled in the art and which are encompassed in the spirit of the disclosure and as defined in the appended claims. While various aspects have been described for purposes of this disclosure, various changes and modifications may be made which are well within the scope of the disclosure. Numerous other changes may be made which will readily suggest themselves to those skilled in the art and which are encompassed in the spirit of the disclosure and as defined in the claims.

What is claimed is:

1. An endoscope having a proximal end and a distal end with a steerable distal tip, the endoscope comprising:

a motor positioned within an interior of the endoscope, the motor comprising an axle aligned substantially parallel to a long axis of the endoscope;

a drum connected to the axle such that rotation of the axle causes rotation of the drum about an axis parallel to the long axis of the endoscope;

an anchoring cylinder affixed to an interior surface of the endoscope;

a first pull wire coupled to the drum and affixed to the anchoring cylinder, such that rotation of the drum in a first direction causes the first pull wire to wind around the drum; and a second pull wire coupled to the drum and affixed to the anchoring cylinder, such that rotation of the drum in a second direction causes the second pull wire to wind around the drum.

2. The endoscope of claim 1, wherein the drum comprises:

a first winding port through which the first pull wire is threaded; and a second winding port through which the second pull wire is threaded.

3. The endoscope of claim 2, wherein the anchoring cylinder comprises:

a first anchoring port through which the first pull wire is threaded; and a second anchoring port through which the second pull wire is threaded.

4. The endoscope of claim 1, wherein the first pull wire and the second pull wire are affixed to the anchoring cylinder with an adhesive.

5. The endoscope of claim 1, wherein the endoscope further comprises an electrical interface positioned proximal from the motor.

6. The endoscope of claim 1, wherein a maximum diameter of the motor is less than 6 mm.

7. An endoscope comprising:

a proximal end housing a drive system;

a distal end including a steerable distal tip;

a first pull wire having a proximal end, coupled to the drive system, and a distal end affixed to the steerable distal tip; and a second pull wire having a proximal end, coupled to the drive system, and a distal end affixed to the steerable distal tip;

wherein the drive system comprises:

a motor positioned within an interior of the endoscope, the motor comprising an axle aligned substantially parallel to a long axis of the endoscope;

a drum connected to the axle such that rotation of the axle causes rotation of the drum about an axis parallel to the long axis of the endoscope, wherein:

the proximal ends of the first pull wire and the second pull wire are coupled to the drum;

rotation of the drum in a first direction causes the distal tip to bend in a first direction; and rotation of the drum in a second direction causes the distal tip to bend in a second direction.

8. The endoscope of claim 7, wherein the drum comprises:

a first winding port through which the first pull wire is threaded; and a second winding port through which the second pull wire is threaded.

9. The endoscope of claim 7, further comprising: an anchoring cylinder affixed to the endoscope, wherein the proximal ends of the first pull wire and the second pull wire are affixed to the anchoring cylinder, wherein the anchoring cylinder comprises:

a first anchoring port through which the first pull wire is threaded; and a second anchoring port through which the second pull wire is threaded.

10. The endoscope of claim 9, wherein a diameter of the drum is less than a diameter of the anchoring cylinder.

11. The endoscope of claim 7, wherein a maximum outer diameter of the proximal end and the distal end of the endoscope is less than 6 mm.

12. A drive system housed within an endoscope, the drive system comprising:

a first motor comprising a first axle aligned substantially parallel to a long axis of the endoscope;

a first drum connected to the first axle such that rotation of the first axle causes rotation of the first drum, wherein the first drum comprises a first winding port to receive a first pull wire and a second winding port to receive a second pull wire;

a first anchoring cylinder comprising a first anchoring port to receive the first pull wire and a second anchoring port to receive the second pull wire;

a second motor positioned proximal from the first motor, comprising a second axle aligned substantially parallel to a long axis of the endoscope;

a second drum connected to the second axle such that rotation of the second axle causes rotation of the second drum, wherein the second drum comprises a third winding port to receive a third pull wire and a fourth winding port to receive a fourth pull wire; and a second anchoring cylinder comprising a third anchoring port to receive the third pull wire and a fourth anchoring port to receive the fourth pull wire.

13. The drive system of claim 12, wherein the first motor and the second motor have a maximum diameter of less than 6 mm.

14. The drive system of claim 12, further comprising an electrical interface coupled to electrical connections of the first motor and the second motor.

15. The drive system of claim 12, wherein:

rotation of the first drum in a first direction causes a steerable tip of the endoscope to bend in a first direction;

rotation of the first drum in a second direction causes the steerable tip to bend in a second direction;

rotation of the second drum in the first direction causes the steerable tip to bend in a third direction; and rotation of the second drum in the second direction causes the steerable tip to bend in a fourth direction.

* * * * *